United States Patent [19]
Hanrahan et al.

[11] Patent Number: 5,105,453
[45] Date of Patent: Apr. 14, 1992

[54] WOOD POLE DECAY DETECTOR

[76] Inventors: Robert C. Hanrahan, 3 Lockridge Street, Whitby, Ontario, Canada, L1R 1C5; Herman Alfermann, 11 Sawyer Cresc., Markham, Ontario, Canada, L3P 5V2

[21] Appl. No.: 618,958

[22] Filed: Nov. 28, 1990

[51] Int. Cl.$^5$ ............................................. G01B 15/06
[52] U.S. Cl. ........................................ 378/58; 378/210
[58] Field of Search ............................................ 378/58

[56] References Cited
U.S. PATENT DOCUMENTS

| | | |
|---|---|---|
| 3,136,892 | 6/1964 | Willett ................................. 378/58 |
| 3,460,152 | 8/1969 | Proctor . |
| 3,594,579 | 7/1971 | Garrett . |
| 3,864,627 | 2/1975 | Shigo . |
| 3,877,294 | 4/1975 | Shaw . |
| 3,946,234 | 3/1976 | Hounsfield . |
| 4,283,629 | 8/1981 | Habermehl . |
| 4,399,701 | 8/1983 | Dunlop . |

FOREIGN PATENT DOCUMENTS 424005  4/1974  U.S.S.R. .
765654  9/1980  U.S.S.R. .

OTHER PUBLICATIONS

"Nondestructive Evaluation of Wood Utility Poles--vol. 1: Current Status"-Mar. 1987.
"CAT Scanner Inspects Poles in Field"-Transmission & Digest Magazine-Aug. 1989.

Primary Examiner—Craig E. Church
Attorney, Agent, or Firm—Ridout & Maybee

[57] ABSTRACT

A manually operable device for detecting wood pole decay and a method of using the same are disclosed. A gamma ray emitter is provided with guide means enabling it to be piloted longitudinally along the wooden pole so that gamma rays from the emitter pass diametrically through the wooden pole along a longitudinal axis of the pole. The attenuation of the gamma rays are continuously recorded along the longitudinal axis, and a permanent record of the variation in gamma ray attenuation is made, from which it can be determined whether the pole is healthy or decayed, and if decayed, the location of the decay along the pole. In order to facilitate locating decay in the pole, the guide means includes an odometer programmed to provide an electrical pulse every 15 cm which is recorded with the data of gamma ray attenuation. Once data on gamma ray attenation has been recorded along one longitudinal axis of the pole, the device may be used on a longitudinal axis at 90° to the first axis, in order to pinpoint the latitude and extent of decay points in the wooden pole.

16 Claims, 4 Drawing Sheets

WOOD POLE DECAY DETECTOR

BACKGROUND OF THE INVENTION

1. Field of the Invention

This invention is directed to a device employing the principle of gamma ray attenuation for determining the presence and location of decay in wooden poles, such as wood utility poles.

2. Description of the Related Art

Wood utility poles are still one of the preferred structures for supporting telephone and electrical transmission wires, and are selected to withstand a horizontal force applied two feet from the top of the pole when supported at the normal groundline. It has been found that this type of horizontal load produces a moment on the wood pole that results in the stress being concentrated at or near groundline. In the case of a 35 foot pole with a set of 6 feet the relative stress over the bottom 5 feet is shown as follows:

| Distance Above Groundline (Ft) | Relative Stress |
|---|---|
| 0.0 | 1.00 |
| 0.5 | 0.98 |
| 1.0 | 0.96 |
| 1.5 | 0.94 |
| 2.0 | 0.93 |
| 2.5 | 0.91 |
| 3.0 | 0.89 |
| 3.5 | 0.87 |
| 4.0 | 0.85 |
| 4.5 | 0.83 |
| 5.0 | 0.81 |

Minimum circumferential dimensions of poes at groundline are so determined such that all poles of the same class regardless of length will withstand the same horizontal force. The assumption made is that the maximum bending moment (stress) is at groundline. However, if sufficient decay takes place at a location other than groundline the stress at that location may exceed the modules of rupture (MOR) causing the wood pole to break. For example, if at 5 feet above groundline a wood pole is experiencing 50% decay, the stress concentration would be sufficient to cause failure at this location.

The mathematical expression for internal moments beyond the elastic limit (break or yield point) is:

$$M = S \, I/C$$

where
M = moment at yield point
S = modulus of rupture (MOR)
I/C = Section modulus (moment of inertia of a circular cross section/diameter)

The modulus of rupture is therefore an experimentally determined value and the formula is empirical. The bending moment applied to a wood pole as a result of a horizontal load causes one section to undergo compression the other tension. Therefore there is an equalization of stress over the cross section. The outer material may be expected to develop greater ultimate strength than in simple stress on account of the reinforcing action of the material nearer the centre that has not yet been overstrained. In the case of wood the ultimate strength in tension is approximately one half of the MOR of horizontal bending.

In addition to stress factors caused by load, wood poles in situ are exposed to a number of natural factors, such as weathering, insect infestation and fungus, which may cause decay or rot in the pole, and create a potential hazard in weakening of the pole, especially in the first 5 foot region of greatest load-bearing stress.

One source of decay is ground rot, and to combat this, wood utility poles are generally butt-treated with preservatives. However, such preservative treatment generally extends only about one foot above ground level, and therefore, the decay sources mentioned above, such as constant dampness, insect infestation and fungus may enter the pole above the level of preservative treatment, but still within the region of greatest load-bearing stress, and cause shell-rot around the outside of the pole or decay in the centre of the pole.

It would therefore greatly benefit power distribution design and reliability to be able to detect the presence of decay and determine if a wood pole is still capable of supporting the designed load or increased loads.

The traditional method to determine the presence of decay in wood utility poles is incremental boring, in which a number of taps are mechanically taken from different areas on a pole as samples of the structure. However, incremental boring is time consuming and necessarily inaccurate, especially in the case of either localized decay or decay occurring at the centre of the pole.

It has long been known that gamma rays (electromagnetic radiation of very short wave about $10^{-12}$ cm, and high penetrating power) weaken as they pass through mass. The measurement of gamma ray attenuation in order to determine the density of materials has been used for a number of years, a well known example of which is the development of the CAT scanner for medical diagnosis and research.

The same principle has been applied in field use, to determine the presence of rot or decay in trees and wooden poles, particularly because the path of gamma ray emissions is not affected by magnetic fields.

For example, in U.S. Pat. No. 4,283,629, a device for determining the existence of disease, such as red rot, in living trees is disclosed. The device, which weighs in excess of 50 lbs, can be clamped onto a tree trunk in order to provide a series of readings around the circumference of the trunk at each latitude, and these readings may be reproduced by computer graphics three dimensional image on a computer screen.

Similarly, in an article entitled "CAT Scanner Inspect Poles In Fields", in *Transmission & Distribution* magazine dated August 1989, a similar device has been adapted for use on wooden utility poles, the device requiring hook-up to a computer for the rapid calculation of the thousands of "ray-sums" yielded by rotation of the device around the pole circumference at each level, to reconstruct the pole image.

OBJECTS OF THE INVENTION

It is an object of the present invention to provide a manual scanning device to rapidly determine the presence or absence of decay in a wooden pole.

It is a further object of the present invention to provide a device which is lightweight so as to be operable as a handheld instrument, without the necessity of clamping the device onto the structure being scanned for proper support.

It is a further object of the present invention to provide a method for rapidly scanning a wooden utility pole to determine the presence or absence of decay in the pole, and from such information, to calculate the load bearing capacity of the pole to determine whether a replacement should be made.

SUMMARY OF THE INVENTION

According to the invention, there is provided a manually operable device for detecting wooden pole decay, consisting of a gamma ray emitter, guide means to pilot the emitter longitudinally along a wooden pole while gamma rays from the emitter pass diametrically through the wooden pole, and recording means for receiving the gamma rays and for maintaining a continuous record of attenuation of the gamma rays. According to one embodiment, a gamma ray receiver faces the emitter and is spaced from the emitter to permit the positioning of the emitter and receiver on diametrically opposite sides of the wooden pole.

Preferably, the guide means includes a counter which transmits a signal to the recording mean at constant spacial intervals, and the signal is recorded in the continuous record of attenuation of the gamma rays, so that the exact longitudinal positioning of the decay can be determined from such records.

Also according to the invention, there is provided a method for locating decay in a wooden pole, which consists of the steps of passing a gamma ray laterally through the wooden pole along a first path substantially parallel to the longitudinal axis of the pole, and receiving and recording therefrom, attenuated gamma ray values to the pole, in order to produce a record of the first series of gamma ray attenuation values along the longitudinal axis of the pole, passing the gamma ray laterally through the wooden pole along a second path substantially parallel to the longitudinal axis of the pole but offset from the first path, and receiving and recording therefrom attenuated gamma ray values through the pole, in order to produce a record of a second series of gamma ray attenuation values along the longitudinal axis of the pole, and calculating the average attenuation values along the length of the wooden pole from the records of the first and second series of gamma ray attenuation values. The average attenuation values are then compared with standard attenuation values for non-decayed poles in order to locate decay points in the pole. Preferably, the second longitudinal path is 90° offset from the first longitudinal path.

From the determination of decay points in the pole, the load bearing strength of the pole can be determined.

DETAILED DESCRIPTION OF THE PREFERRED EMBODIMENTS

Figure 1:
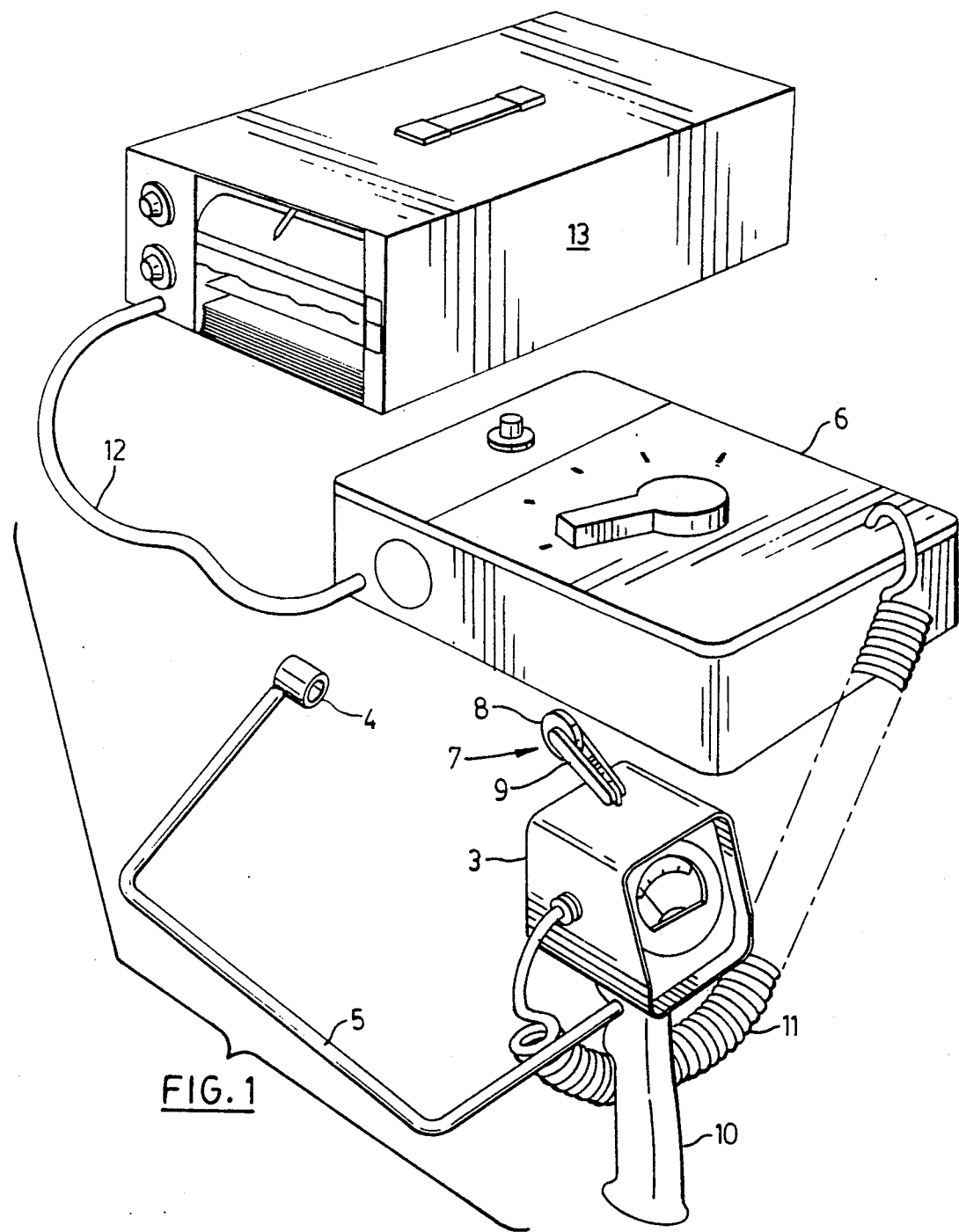
FIG. 1 is a perspective view of a wood pole decay detector, according to the invention.
Figure 2:
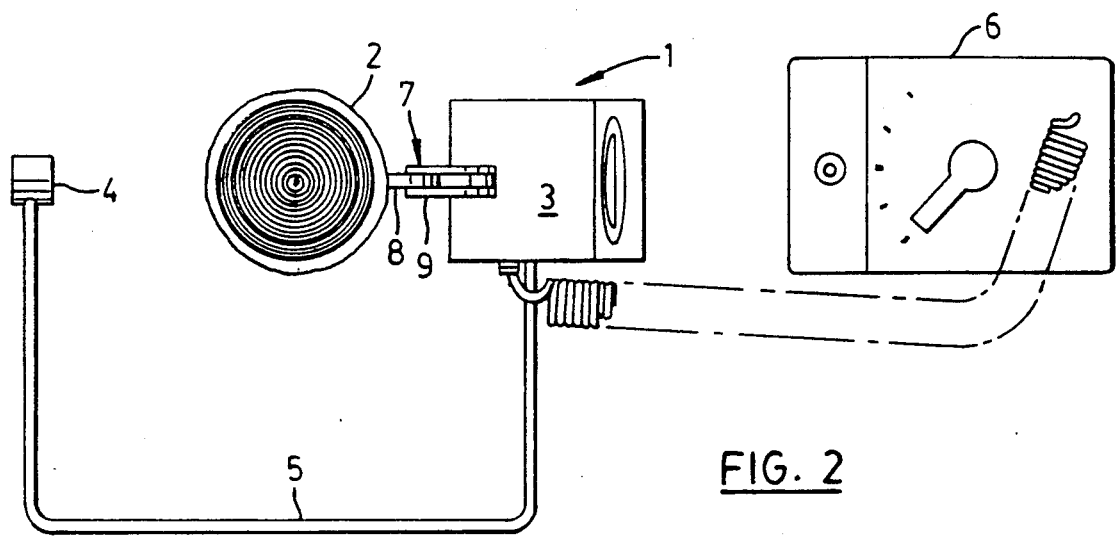
FIG. 2 is a top plan schematic view of a wood pole decay detector, in use.
Figure 3:
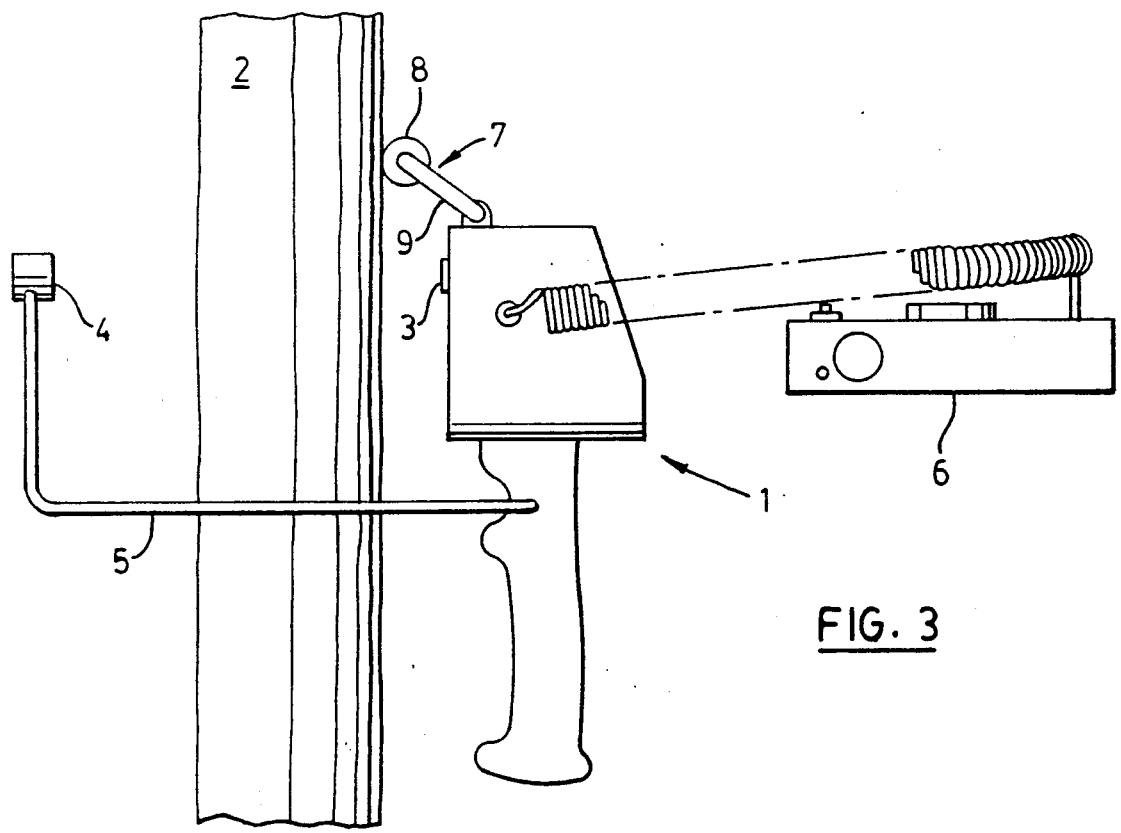
FIG. 3 is a side plan schematic view of the decay detector shown in FIG. 2 in use.

Referring to FIGS. 1, 2 and 3, a wood pole decay detector 1 may be used to measure the amount of decay in a wooden utility pole 2.

The decay detector consists of a gamma ray emitter 3 and an opposed gamma ray receiver or sensor 4 in facing relationship, rigidly connected by a conduit 5 which includes connection means between the receiver/sensor 4 and the emitter 3.

The emitter 3 is, in turn, connected through coiled cord 11 to a transceiver 6 which both powers the emitter and receives a signal transmitted from receiver/sensor 4. External recording means, such as a chart recorder 13 may be remotely connected through wire 12 to the transceiver 6 to receive, store and display the data on gamma ray attenuation sensed by the receiver 4.

A guide means 7, in the form of a rotary member or wheel 8 mounted on an axle 9 connected to the emitter 3, is adapted to emit an electrical pulse every 15 cm, as an odometer wheel. The distance pulse is transmitted through the emitter 3 and cord Il to the transceiver 6, and is recorded with the signal transmitted from the receiver/sensor 4. This is realised in the graphic illustrations of FIGS. 4A, 4B and 4C by the regular pulses 20.

The rotary member 8 of guide means 7 is preferably configured with a tapered etching surface or edge in order to dig into the surface of a wooden utility pole so that the wheel maintains contact with the pole, both to facilitate a steady line of movement of the decay detector along the grain of the pole 2, and to provide an accurate reading of distance travelled along the pole.

A grip 10 mounted on the emitter 3 facilitates manual grasping and positioning of the apparatus.

In use, inspection of a wooden pole for decay is performed by locating the decay detector at one end of the wooden pole through initiating contact between the guide member 7 and the pole surface, and arranging the receiver/sensor 4 on the opposite side of the pole from the emitter 3, as shown in FIGS. 2 and 3.

The decay detector is then slowly moved along the longitudinal axis of the pole such that the rotary member 8 of the guide member 7 rotates by maintaining contact with the wood pole 2.

Figure 4B:
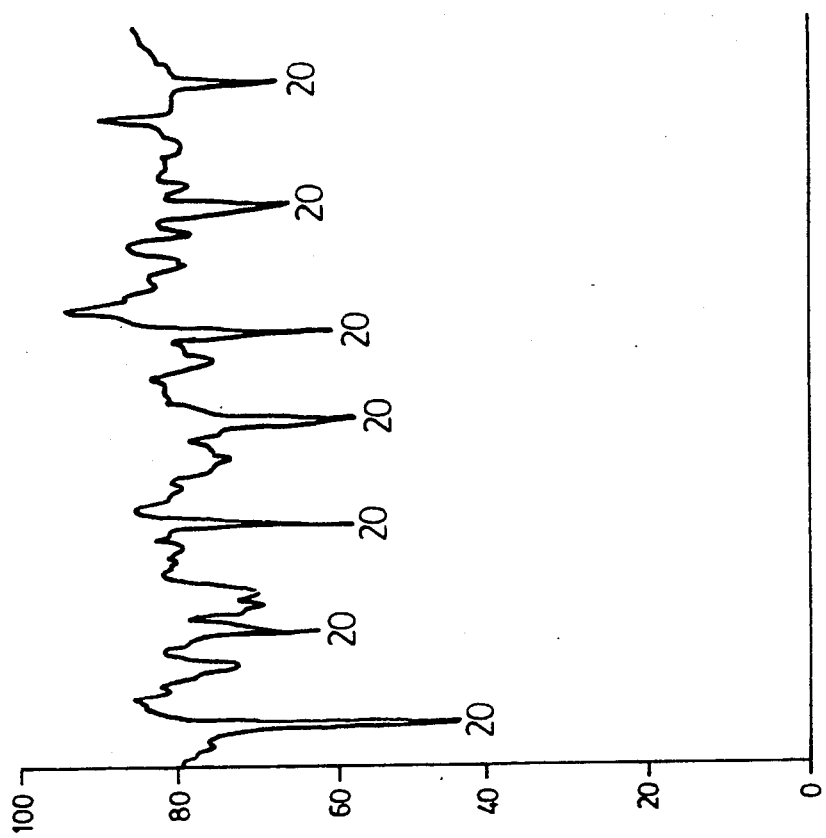
FIGS. 4A and 4B are graphic illustrations of values from the decay detector, in use, indicating healthy and decayed wood in the pole, respectively.
Figure 4A:
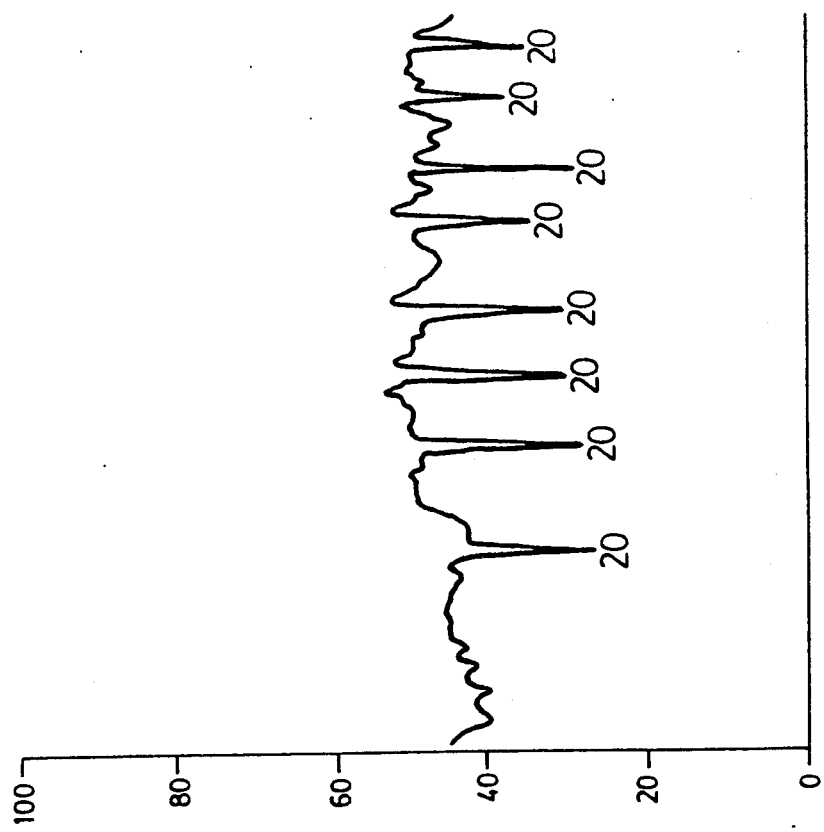
Figure 4C:
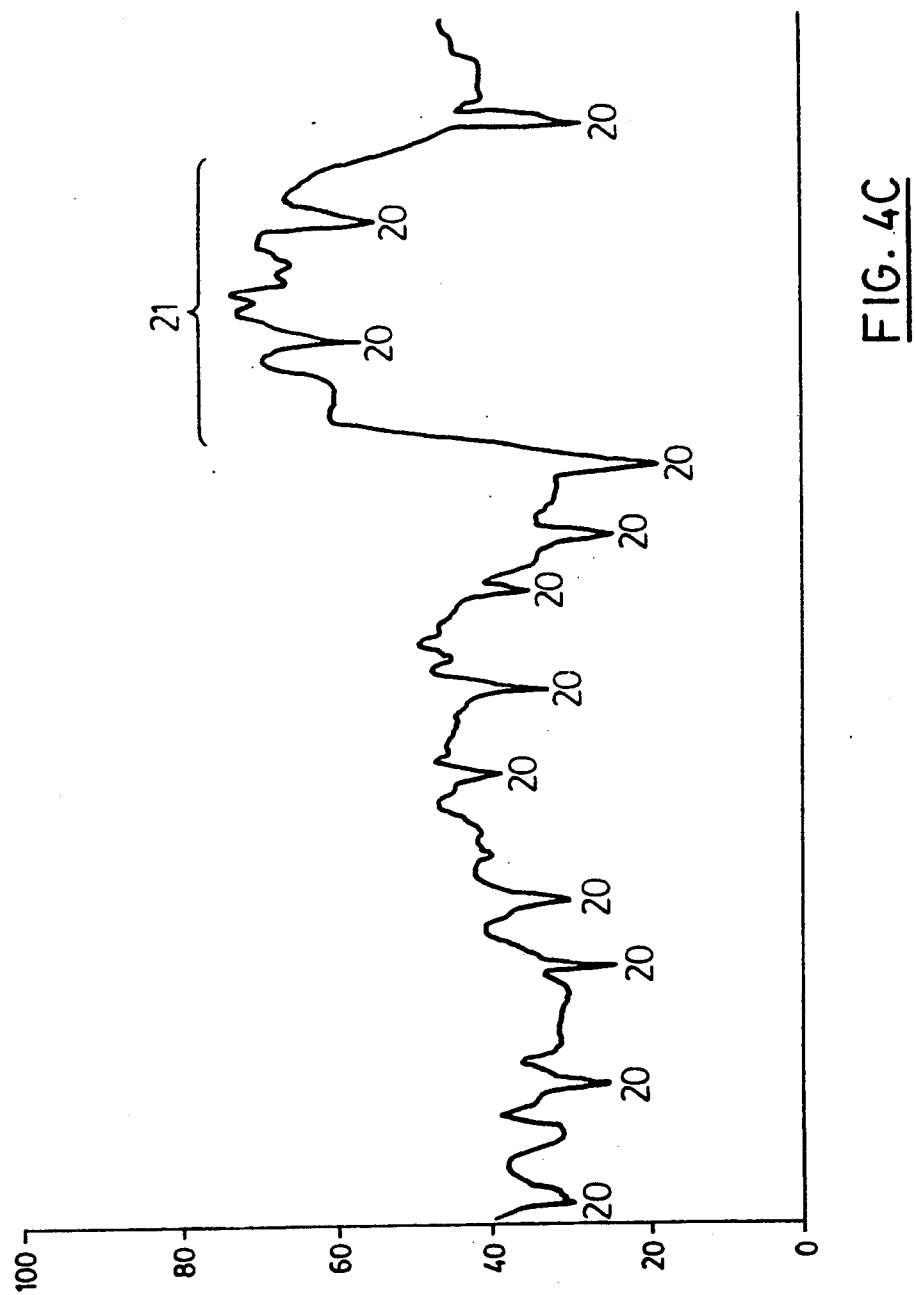
FIG. 4C is a further graphic illustration of values from the decay detector, in use, indicating localised pole decay.

A single gamma ray emitted by the emitter 3 is received by receiver 4 throughout the detector's transit along the length of the pole, and the attenuation of the gamma ray caused by the pole density is transmitted in the form of continuous series of electrical pulses from receiver 4 to transceiver 6 either for electronic storage or for recording on a strip chart of the type illustrated in FIGS. 4A, 4B and 4C. For the purposes of the present invention, it has been found that gamma photons from an Am-241 source at a strength of 25 mrem/hour from the emitter source may be used for sufficiently accurate readings.

The electrical pulse emitted every 15 cm by the guide member 7 is incorporated into and recorded with the gamma ray attenuation data received from receiver 4, so that, in the case of the strip charts of FIG. 4A, 4B and 4C, the electrical pulse 20 every 15 cm clearly indicates the longitudinal distance travelled by the device along the pole.

The wood pole decay detector measures the degree of decay of a wooden pole by comparing the instrument's response during a test to that of a non-decayed specimen, values for non-decayed specimens being lower than those for decayed poles. For example, a wood pole that is decayed by 50% should indicate a 50% higher response than the usual values for a non-decayed pole of that particular type of wood.

Varying pole diameters can be compensated for by measuring the circumference of the wood pole and inputting this information into the transceiver or a remote computer before testing.

The strip charts shown in FIGS. 4A, 4B and 4C illustrate examples of variation in values received through the transceiver 6. FIG. 4A indicates a healthy pole with substantial attenuation or weakening of the gamma ray readings, while FIG. 4B illustrates a decayed pole with much stronger gamma ray readings passing through the less dense decayed wood.

FIG. 4C illustrates the expected shape of readings where a largely healthy pole exhibits localised decay as shown at 21.

As indicated above, the majority of decay occurs in wooden poles a short distance above the ground, generally within the first seven feet, and this is also the area generally subjected to the greatest horizontal loads.

With the present device, it is possible to examine wooden poles in situ. This same device may be used to examine poles prior to installation, in prone position, so as to pre-emptorily reject unsuitable poles.

Where the entire length of a pole in situ is desired to be measured, a cherry picker or other method for smoothly elevating the operator the entire height of the pole, may be used.

When estimating the breaking strength of a wood pole two measurements at right angles to each other are taken from groundline to the desired height. In the following tables (see Examples 1 and 2) the height of inspection was 84 inches. The use of the odometer wheel of guide means 7 allowed the instrument's response to be recorded versus height and the correlation of the right angle inspections to produce an average response.

The average instrument indication (AII) is then divided by the moment of inertia for a circular cross section to produce a relative strength response versus height. By dividing the relative stress (previously described) by the relative strength, the location of breakage and ultimate horizontal load can be predicted.

The location of breakage occurs where the relative stress/relative strength is a maximum.

The ultimate horizontal force is proportional to the relative strength indication at the location of maximum relative stress.

EXAMPLE 1

| Distance Above Groundline (in) | Average Instrument Indication (AII) | AII Moment of Inertia | Relative Stress AII Moment of Inertia |
| --- | --- | --- | --- |
| 0 | 37.5 | 1.244 | 270 |
| 7 | 47.5 | 1.048 | 314 |
| 14 | 59.0 | 0.843 | 381 |
| 21 | 64.0 | 0.778 | 405 |
| 28 | 61.5 | 0.809 | 380 |
| 35 | 69.0 | 0.721 | 417 |
| 42 | 70.0 | 0.711 | 413 |
| 49 | 73.0 | 0.682 | 421* |
| 56 | 68.0 | 0.732 | 382 |
| 63 | 70.0 | 0.711 | 384 |
| 70 | 73.0 | 0.682 | 390 |
| 77 | 73.5 | 0.677 | 382 |

-continued

| Distance Above Groundline (in) | Average Instrument Indication (AII) | AII Moment of Inertia | Relative Stress AII Moment of Inertia |
| --- | --- | --- | --- |
| 84 | 72.5 | 0.686 | 367 |

*location of predicted breaking point 42 to 49 inches location of break 48 inches - horizontal load 550 lbs

EXAMPLE 2

| Distance Above Groundline (in) | Average Instrument Indication (AII) | AII Moment of Inertia | Relative Stress AII Moment of Inertia |
| --- | --- | --- | --- |
| 0 | 57.5 | 0.936 | 359 |
| 7 | 61.0 | 0.882 | 373 |
| 14 | 65.0 | 0.828 | 389* |
| 21 | 66.0 | 0.815 | 386 |
| 28 | 66.0 | 0.815 | 377 |
| 35 | 68.0 | 0.791 | 380 |
| 42 | 66.0 | 0.815 | 360 |
| 49 | 72.5 | 0.742 | 386 |
| 56 | 75.0 | 0.718 | 390 |
| 63 | 75.0 | 0.694 | 380 |
| 70 | 77.5 | 0.694 | 383 |
| 77 | 75.0 | 0.718 | 360 |
| 84 | 80.0 | 0.673 | 374 |

*location of predicted breaking point 7 to 14 inches location of break 8 inches - horizontal load 880 lbs Obvious modifications, such as removal of the grip 10 in order to facilitate measurements directly at ground level and upwards may be employed, and will be obvious to one skilled in the art.

We claim:

1. A manually-operable device for detecting wood pole decay, comprising:
   a gamma ray emitter;
   guide means to pilot the emitter longitudinally along the wooden pole while gamma rays from the emitter pass diametrically through the wooden pole; and
   recording means for receiving the gamma rays through the wooden pole and for maintaining a continuous record of attenuation of the gamma rays.

2. A manually operable device, according to claim 1, wherein the guide means further comprises a counter adapted to transmit a signal to the recording means at constant spacial intervals, and wherein the recording means records said signal in the continuous record of attenuation of the gamma rays.

3. A manually operable device for detecting wood pole decay, comprising:
   a gamma ray emitter;
   a gamma ray receiver facing the emitter and spaced from the emitter to permit positioning of the emitter and receiver on diametrically opposite sides of a wooden pole;
   guide means to pilot the emitter and receiver longitudinally along the wooden poles while gamma rays from the receiver pass diametrically through the wooden pole to the receiver; and
   recording means connected to the receiver for maintaining a continuous record of attenuation of the gamma rays.

4. A manually operable device, according to claim 3, wherein the guide means further comprises a counter adapted to transmit a signal to the recording means at constant spacial intervals, and wherein the recording means records said signal in the continuous record of attenuation of the gamma rays.

5. A manually operable device, according to claim 3, further comprising rigid connection means between the emitter and receiver for maintaining said emitter and receiver in constant fixed relation.

6. A manually operable device, according to claim 5, wherein the guide means comprise a member having a etching surface adapted to be directed in contact with the wooden pole.

7. A manually operable device, according to claim 6, wherein the guide means is a rotary member affixed to and adapted to precede the emitter in rolling contact longitudinally along the pole.

8. A manually operable device, according to claim 7, wherein the guide means connected to the recording means and is adapted to transmit a pulse to the recording means on each rotation of the rotary member, and wherein the recording means records said pulse in the continuous record of attenuation of the gamma rays.

9. A manually operable device, according to claim 3, wherein the emitter is mounted on a hand grip.

10. A manually operable device, according to claim 3, wherein the recording means further comprises calculating means for determining the location of decay in the wooden pole from the record of attenuation of the gamma rays.

11. A manually operable device, according to claim 10, wherein the calculating means comprises a display integral with the gamma ray emitter.

12. A manually operable device, according to claim 10, further comprising a display remotely located from the calculating means.

13. A method for locating decay in a wooden pole, comprising the steps of:
passing a gamma ray laterally through the wooden pole along a first path substantially parallel to the longitudinal axis of the pole, and receiving and recording therefrom attenuated gamma ray values through the pole, whereby to produce a record of a first continuous series of gamma ray attenuation values along the longitudinal axis of the pole;
passing the gamma ray laterally through the wooden pole along a second path substantially parallel to the longitudinal axis of the pole, but offset from the first path, and receiving and recording therefrom attenuated gamma ray values through the pole, whereby to produce a record of a second continuous series of gamma ray attenuation values along the longitudinal axis of the pole;
calculating average attenuation values along the length of the wooden pole from the records of the first and second series of gamma ray attenuation values; and
comparing the average attenuation values along the length of the wooden pole with standard attenuation values for non-decayed poles, whereby to locate decay points in the pole.

14. A method for locating decay in a wooden pole, according to claim 13, wherein the second path is substantially 90° offset from the first path.

15. A method for locating decay in a wooden pole, according to claim 14, further comprising the steps of:
marking constant spacial intervals as the gamma ray passes along each of the first and second paths; and
recording said constant spacial intervals in the records of the first and second series of gamma ray attenuation values and said average attenuation values.

16. A method for locating the decay in a wooden pole, according to claim 15, further comprising the steps of:
calculating horizontal load of decay points in the pole; and
calculating load-bearing strength of the pole with reference to the horizontal loads at the decay point in the pole.

* * * * *